US009440889B2

(12) United States Patent
Ingels (10) Patent No.: US 9,440,889 B2
(45) Date of Patent: Sep. 13, 2016

(54) PROCESSES AND PLANTS FOR REDUCING AMMONIA LOSS AND ODOR FROM ORGANIC MATERIAL OR WASTE TO THE ATMOSPHERE (71) Applicant: N2 Applied AS, Oslo (NO)

(72) Inventor: Rune Ingels, Svene (NO)

(73) Assignee: N2 APPLIED AS, Oslo (NO)

( * ) Notice: Subject to any disclaimer, the term of this patent is extended or adjusted under 35 U.S.C. 154(b) by 47 days.

(21) Appl. No.: 14/351,676

(22) PCT Filed: Dec. 10, 2012

(86) PCT No.: PCT/NO2012/050245
§ 371 (c)(1),
(2) Date: Apr. 14, 2014

(87) PCT Pub. No.: WO2013/085395
PCT Pub. Date: Jun. 13, 2013

(65) Prior Publication Data
US 2015/0299056 A1    Oct. 22, 2015

(30) Foreign Application Priority Data
Dec. 8, 2011    (NO) .................................. 20111701

(51) Int. Cl.
| C05B 17/00 | (2006.01) |
| A61L 9/14 | (2006.01) |
| A61L 9/22 | (2006.01) |
| A61L 11/00 | (2006.01) |
| B01D 53/32 | (2006.01) |
| B01D 53/58 | (2006.01) |
| C05C 1/00 | (2006.01) |
| C05F 3/00 | (2006.01) |
| C12M 1/107 | (2006.01) |
| C12M 1/00 | (2006.01) |
| C05F 17/00 | (2006.01) |
| B01J 19/08 | (2006.01) |
| B01J 19/12 | (2006.01) |
| B03C 3/017 | (2006.01) |
| C05G 3/08 | (2006.01) |

(52) U.S. Cl.
CPC ............... *C05B 17/00* (2013.01); *A61L 9/145* (2013.01); *A61L 9/22* (2013.01); *A61L 11/00* (2013.01); *B01D 53/323* (2013.01); *B01D 53/326* (2013.01); *B01D 53/58* (2013.01); *B01J 19/088* (2013.01); *B01J 19/126* (2013.01); *B01J 19/129* (2013.01); *B03C 3/017* (2013.01); *C05C 1/00* (2013.01); *C05F 3/00* (2013.01); *C05F 17/0054* (2013.01); *C05G 3/08* (2013.01); *C12M 21/04* (2013.01); *C12M 47/18* (2013.01); *A61L 2209/213* (2013.01); *B01D 2251/2062* (2013.01); *B01D 2257/406* (2013.01); *B01D 2257/90* (2013.01); *B01D 2258/0266* (2013.01); *B01J 2219/0805* (2013.01); *B01J 2219/0875* (2013.01); *B01J 2219/0894* (2013.01); *B01J 2219/1206* (2013.01); *Y02C 20/20* (2013.01); *Y02E 50/343* (2013.01); *Y02P 20/145* (2015.11); *Y02W 30/43* (2015.05); *Y02W 30/47* (2015.05)

(58) Field of Classification Search
None
See application file for complete search history.

(56) References Cited

U.S. PATENT DOCUMENTS

| 2,485,476 | A | | 10/1949 | Cotton | |
| 3,966,450 | A | | 6/1976 | O'Neill et al. | |
| 4,031,187 | A | * | 6/1977 | Barba | C01B 21/26 423/392 |
| 4,139,595 | A | * | 2/1979 | Vaseen | B01D 53/56 204/177 |
| 4,141,715 | A | * | 2/1979 | Wyse | C05C 11/00 204/179 |
| 4,205,054 | A | * | 5/1980 | Sugahara | C01B 21/42 423/390.1 |
| 4,219,534 | A | * | 8/1980 | Ethington | C01C 1/185 423/235 |
| 4,219,536 | A | * | 8/1980 | Hoenke | B01D 53/56 423/393 |
| 4,233,279 | A | * | 11/1980 | Balint | C01B 21/50 423/235 |
| 4,297,123 | A | | 10/1981 | Wyse et al. | |
| 5,192,355 | A | * | 3/1993 | Eastin | C01B 21/26 423/359 |
| 5,378,257 | A | * | 1/1995 | Higashida | C05F 9/00 210/205 |
| 5,976,211 | A | * | 11/1999 | Fjelldal | C05C 11/00 71/11 |
| 6,193,934 | B1 | * | 2/2001 | Yang | B01D 53/56 422/169 |
| 6,277,344 | B1 | | 8/2001 | Hei et al. | |
| 7,785,388 | B2 | | 8/2010 | Hartmann et al. | |
| 7,909,995 | B2 | | 3/2011 | Jiang et al. | |
| 2009/0193863 | A1 | * | 8/2009 | Szogi | C05B 17/00 71/21 |
| 2011/0044927 | A1 | | 2/2011 | Weschler | |

FOREIGN PATENT DOCUMENTS

| CA | 2 757 119 | 10/2010 |
| CN | 1621743 | 6/2005 |

(Continued)

OTHER PUBLICATIONS

International Search Report dated Apr. 2, 2013 issued in International (PCT) Application No. PCT/NO2012/050245.

(Continued)

*Primary Examiner* — Melvin C Mayes
*Assistant Examiner* — Sheng H Davis
(74) *Attorney, Agent, or Firm* — Wenderoth, Lind & Ponack, L.L.P.

(57) ABSTRACT

The invention relates to processes for reducing ammonia loss and odor from organic material or waste to the atmosphere. A plasma generator is applied to upgrade organic waste and manure with a mixture of acidic nitrates and nitrites. The present invention also relates to an acidic nitrate solution, suitable for reducing ammonia loss and odor from organic material or waste to the atmosphere, and a process for producing such an acidic nitrate solution. The invention further comprises plants for reducing ammonia loss and odor from organic material or waste to the atmosphere.

17 Claims, 2 Drawing Sheets

(56) References Cited

FOREIGN PATENT DOCUMENTS

| CN | 1772347 | 5/2006 |
|---|---|---|
| CN | 1903705 | 1/2007 |
| DK | 2006 00530 | 4/2006 |
| EP | 0 637 577 | 7/1994 |
| EP | 1 314 698 | 6/2006 |
| JP | 2006-247522 | 9/2006 |
| RU | 2 004 529 | 12/1993 |
| RU | 2004529 | 12/1993 |
| SE | 366 730 | 9/1972 |
| SE | 513 574 | 10/2000 |
| WO | 03/014016 | 2/2003 |
| WO | 2006/026723 | 3/2006 |
| WO | 2009/059615 | 5/2009 |
| WO | 2009059615 | * 5/2009 |
| WO | 2010/114580 | 10/2010 |

OTHER PUBLICATIONS

Office Action issued Nov. 4, 2015 in corresponding Chinese Application No. 201280059720.4, with English translation.
UNIDO and IFDC "Fertilizer Manual", 1998, 3rd ed., pp. 209-226.
Wuping Chen, Inorganic Chemical Technology, Apr. 2002, 3rd edition, pp. 342-343.

* cited by examiner

PROCESSES AND PLANTS FOR REDUCING AMMONIA LOSS AND ODOR FROM ORGANIC MATERIAL OR WASTE TO THE ATMOSPHERE

TECHNICAL FIELD

The invention relates to a process for reducing ammonia loss and odor from organic material or waste to the atmosphere, comprising feeding air or contaminated air to a plasma generator to produce a concentration of 0.1-12% by volume of NOx in the air by direct nitrogen fixation, absorbing the NOx into an absorption liquid to form an acidic nitrogen solution, and feeding the solution to the organic material or waste. The present invention also relates to a process for reducing ammonia loss and odor from organic material or waste to the atmosphere, comprising feeding air or contaminated air to a plasma generator to produce a concentration of 0.1-12% by volume of NOx in the air by direct nitrogen fixation, absorbing the NOx into an absorption liquid to form an acidic nitrogen solution, using the solution to scrub ammonia gas from the organic material or waste, and feeding the solution to the organic material or waste. The invention further comprises plants for reducing ammonia loss and odor from organic material or waste to the atmosphere.

BACKGROUND OF THE INVENTION

Prior art has not been able to solve the ammonia loss related environmental challenges in manure and organic waste treatment by applying and combining the technical elements of the present invention. The ammonia loss from manure and organic waste is addressed and tried to be solved by applying various chemicals of acidic character. NOx containing gases generated by a plasma generator has been applied directly to the manure and or organic waste. The method is impractical and unable to control the chemistry in the manure and may introduce a NOx emission issue. If standard nitric acid or salts of nitrate is applied to the manure it is creating loss of nitrogen in the form of $N_2$ and $N_2O$. Odor has been treated with many standard odor suppressing agents. Ammonia emissions and effluents have been reduced through thermal stripping and subsequent absorption by means of a suitable mineral or organic acid. Applying airing and oxygen rich mineral acids like sulfuric and phosphoric acids has reduced the ammonia loss but not helped the nutrient balance nor helped the $N_2O$ emissions. Adding a mixture of nitric acid and nitrous acid to the manure is addressing the nutrient ratio and the nitrogen loss, but has been considered risky from a transport and handling point of view and is normally expensive.

SE 366730 is describing a method where nitric acid, nitrous acid, copper sulfate and other acidic components are used to reduce odor and ammonia losses from manure. The pH in the manure is controlled to be below 7. The safety and cost aspects are making the technique unattractive. Nitric Acid is both a strong acid and a component for explosives. Nitrous acid as a product is instable and component for explosives.

U.S. Pat. No. 7,909,995 is describing how $NH_3$ from manure and organic waste can be absorbed in water with sulfuric acid, forming ammonium sulfate in a standard process based on known industrial techniques. The use of sulfuric acid is not addressing the nutrient balance and nitrate to nitrite ratio. The product is ammonium sulfate solution, which can be crystallized.

U.S. Pat. No. 4,297,123 is describing an electric arc process for fixing nitrogen from air and absorbing it in water with the clear aim of producing Nitrate fertilizers in various forms. The technique is describing the reaction from NO gas oxygen and water to Nitrate, and the design is clearly aimed at producing a pure nitrate in solution and for nitrate fertilizers in small scale based on electricity.

US 2011/0044927 describes a process for odor reduction using metal acetates, nitrates or sulfates for reduction of $H_2S$. The process is addressing the odor issue, but the applied nitrate is taken in as an unsafe and expensive chemical. The use of Nitrate alone will give loss of nitrogen as $N_2$ and $N_2O$. The $N/P_2O_5$ ratio is not focused.

U.S. Pat. No. 7,785,388 describes applying calcium cyanide for reducing odors and enhancing fertilizer value and practical handling. The method is not addressing nor solving the nutrient balance and nitrate to nitrite ratio.

U.S. Pat. No. 6,277,344 describes treating waste off gasses with a peroxy acid in a chemical scrubber. The method is an end of pipe solution which is not addressing the main loss and nutrient balance issue.

DK200600530 describes a method using nitric acid and a plant extract to suppress ammonia and odor from pigsty waste water to reduce hazards. The method is focusing on the hazards and is not solving the nutrient balance and not addressing the nitrite to nitrate ratio. The method will give loss of nitrogen as $N_2$ and $N_2O$.

RU2004529 describes obtaining organomineral fertilizer as follows. Ammonia-containing farm waste is treated with nitrous gas obtained by fixing atmospheric $N_2$ in a low temp. plasma and cooled to below 40 deg. This converts the ammoniacal nitrogen to non-volatile compounds. The method is blowing hot nitrous gas to remove ammonia which is volatile, followed by drying and sterilizing the product. The method is not focusing on the nutrient balance and will not be able to control the critical nitrite to nitrate ratio. The method will create a gaseous emission of NOx and Ammonia.

JP 2006247522 describes a process for incinerating elec. discharge plasma generated evenly and stably in the discharge chamber and waste gases (e.g. incinerator flue gases, malodorous gases in wastewater treatment facilities and municipal refuse treatment facilities, waste gases from chemical plants) are efficiently detoxicated and deodorized. The method is an arc incinerator for cracking smelly components, and is not addressing the nutrient balance or the nitrate to nitrite ratio.

WO 2009059615 A1 is describing a process where a part of the ammonia from organic material is stripped out and converted to nitric acid through a standard combustion and absorption process. The nitric acid produced from the ammonia is then used to react with the remaining ammonia, giving ammonium nitrate.

The remaining challenges can be summarized in the following points:

1) All organic materials contain chemically bound nitrogen. This nitrogen is in the form of ammonia typically from urea, uric acid and proteins. Organic waste is nutrients and energy on the way to be lost. The main way to recover the nutrients has been to recycle the organic waste and manure back to the fields as fertilizer. This practice has reduced the demand for phosphate fertilizer by 30-40% inside the EU over the last 20 years. However, the nitrogen is still being lost in the mineralization process. The loss is coming from the microbial activity releasing free ammonia, where 30% is lost to air and 10% is lost to water through leaching.

The loss reaction from urine starts with hydrolyzation of urea which is described in equation Ia, and the general mineralization of organic material results in ammonium carbonates, aqueous ammonia and carbonic acid which is lost as volatile ammonia and carbon dioxide as in equation Ib.

The carbon dioxide is very volatile and is directly lost to the air, resulting in an increased pH to 9-10 and the subsequent loss of the volatile ammonia.

2) The N to $P_2O_5$ ratio in organic material is too low for a balanced fertilization. The content of nitrogen should typically be doubled in order to meet the nutrient demand of the majority of crops.

3) The ammonia emissions and $N_2O$ emissions from manure processing and storage and after field application is a main contribution to global warming. The ammonia emitted from agriculture is getting oxidized to nitrates which create acidic rain, nitrification, and eutrophication and finally de-nitrification. In all these biological processes formation of $N_2O$ takes place and the $N_2O$ formation has in certain biotopes' been estimated to 3-4% of the ammonia lost.

4) Odor from organic waste is originating mainly from the biological formation of $H_2S$ and others sulfur components. The lack of oxygen in organic waste and manure is giving the basis for $H_2S$ and organic sulfur components with strong odors.

5) The cost and safety aspect of making the right mixture of nitrate, nitrite in the right ratio and concentration has been considered unsafe and costly. The nitrite as a chemical is not commercially available as it is instable in higher concentrations and at higher ambient temperatures. Nitric acid is a strong acid and a component for explosives, making it expensive and risky to transport and store.

The ammonia loss of 30-40% from the meat and dairy production must be compensated from industrially produced ammonia. The production and logistic cost of this ammonia is creating additional greenhouse gas emissions in the form of $CO_2$ and $N_2O$. The global industrial production of mineral fertilizer does actually correspond to the loss from all domesticated animal activity.

For every tonne of ammonia captured, the following GHG emission savings can be made:

| | |
|---|---|
| 1) Nitrification giving 0.35%-2% $N_2O$ | 1.33-7.5 tonne $CO_2$ eq |
| 2) De-nitrification giving 0.35%-2% $N_2O$ | 1.33-7.5 tonne $CO_2$ eq |
| 3) Production of new ammonia | 1.70 tonne $CO_2$ eq |
| 4) Production of nitric acid with 10 ppm $N_2O$ emission | 0.30 tonne $CO_2$ eq |
| 5) Road transport 200 km giving $CO_2$ emissions | 3.00 tonne $CO_2$ eq |
| Total reduction in $CO_2$ equivalents | 7.7-20 tonne $CO_2$ eq. |

The present invention provides a solution to the above challenges.

SUMMARY OF THE INVENTION

The present invention relates to a process for reducing ammonia loss and odor from organic material or waste to the atmosphere, comprising feeding air or contaminated air to an electric arc, electrostatic field, Nano pulsed electric field, dielectric barrier discharged, laser, radio- or micro-wave driven plasma generator, or any combination thereof, to produce a concentration of 0.1-12% by volume of NOx in the air by direct nitrogen fixation;

feeding the air containing NOx to an absorber, and absorbing the NOx into an absorption liquid in the absorber to form an acidic nitrogen solution comprising nitrates and nitrites; and feeding the acidic nitrogen solution to the organic material or waste whereby the pH is adjusted to 4-6 and the nitrates and nitrites bind volatile ammonia and ammonia components in or from the organic material or waste, as ammonium nitrate and nitrite salts.

In an embodiment, the above process comprises feeding air or contaminated air to an electric arc, electrostatic field, Nano pulsed electric field, dielectric barrier discharged, laser, radio- or micro-wave driven plasma generator, or any combination thereof, to produce a concentration of 0.1-12% by volume of NOx in the air by direct nitrogen fixation and subsequent quenching to between 60 and 150° C. within $10^{-3}$ seconds or preferably within $10^{-4}$ seconds, or most preferably $10^{-5}$ seconds; feeding the air containing NOx to an absorber after a retention time of 15 seconds to give a $NO/NO_2$ mole ratio of 3 or preferably after a retention time of 30 seconds to give a $NO/NO_2$ mole ratio of 1.2 or most preferably after a retention time of 60 seconds to get a $NO/NO_2$ mole ratio of 0.95, and absorbing the NOx into an absorption liquid in an absorber operating at a temperature between 20° C. and 80° C., or preferably between 30° C. and 60° C. to form an acidic nitrogen solution comprising nitrates and nitrites; and feeding the acidic nitrogen solution to the organic material or waste whereby the pH is adjusted to 4-6 and the nitrates and nitrites bind volatile ammonia and ammonia components in or from the organic material or waste, as ammonium nitrate and nitrite salts.

In the above process, the acidic nitrogen solution can also be passed through a scrubber to absorb ammonia from ammonia contaminated ventilation air from the organic material or waste.

The present invention also relates to a process for reducing ammonia loss and odor from organic material or waste to the atmosphere, comprising feeding air or contaminated air to an electric arc, electrostatic field, Nano pulsed electric field, dielectric barrier discharged, laser, radio- or micro-wave driven plasma generator, or any combination thereof, to produce a concentration of 0.1-12% by volume of NOx in the air by direct nitrogen fixation;

feeding the air containing NOx to an absorber, and absorbing the NOx into an absorption liquid in the absorber to form an acidic nitrogen solution comprising nitrates and nitrites;

using the acidic nitrogen solution in a scrubber to absorb ammonia from ammonia contaminated ventilation air from the organic material or waste and to produce an acidic ammonium nitrate and nitrite solution; and feeding the acidic ammonium nitrate and nitrite solution produced in the scrubber to the organic material or waste.

In an embodiment, the above process comprises feeding air or contaminated air to an electric arc, electrostatic field, Nano pulsed electric field, dielectric barrier discharged, laser, radio- or micro-wave driven plasma generator, or any combination thereof, to produce a concentration of 0.1-12% by volume of NOx in the air by direct nitrogen fixation and subsequent quenching to between 60 and 150° C. within $10^{-3}$ seconds or preferably within $10^{-4}$ seconds, or most preferably $10^{-5}$ seconds; feeding the air containing NOx to an absorber, after a retention time of 15 seconds to give a $NO/NO_2$ mole ratio of 3 or preferably after a retention time of 30 seconds to give a $NO/NO_2$ mole ratio of 1.2 or most preferably after a retention time of 60 seconds to get a $NO/NO_2$ mole ratio of 0.95, and absorbing the NOx into an absorption liquid in an absorber operating at a temperature between 20° C. and 80° C., or preferably between 30° C. and 60° C. to form an acidic nitrogen solution comprising nitrates and nitrites; using the acidic nitrogen solution in a scrubber to absorb ammonia from ammonia contaminated ventilation air from the organic material or waste and to produce an acidic ammonium nitrate and nitrite solution; and feeding the acidic ammonium nitrate and nitrite solution produced in the scrubber to the organic material or waste. In this process, the organic material or waste can be treated in a bio gas reactor before feeding the acidic ammonium nitrate and nitrite solution produced in the scrubber to the organic material or waste.

In an embodiment of the above processes, air or contaminated air is fed to the plasma generator to produce a concentration of 2-12% by volume of NOx in the air by direct nitrogen fixation.

In a further embodiment of the above processes, the absorption liquid is water or urine.

In a further embodiment of the above processes, the absorption liquid is cold water in excess.

In a further embodiment of the above processes, the organic material or waste is selected from livestock manure and biogas plant rest.

In a further embodiment of the above processes, the nitrate and nitrite components are providing oxygen which suppresses the activity of sulfate reduction to $H_2S$.

In a further embodiment of the above processes, the nitrate and nitrite ratio in combination with a pH of 4-6 is used to disinfect organic materials or waste.

In a further embodiment of the above processes, the molar ratio of nitrite to nitrate is kept between 1/10 and 1/100 which is inhibiting $N_2O$ being formed in the biological nitrification of ammonia.

In a further embodiment of the above processes, the molar nitrate concentration is balancing the molar free ammonia-N concentration to improve the plant uptake rate of nitrogen.

In a further embodiment of the above processes, the plasma generator is used to incinerate and disinfect contaminated air by exposing the contaminants to plasma and electron bombardment.

In a further embodiment of the above processes, the nitrate and nitrite solution is used to improve the agronomic availability of the phosphate, through a temporary lowering of pH to 4 which is dissolving and mobilizing the colloidal phosphates precipitates.

In a further embodiment of the above processes, the acidic nitrogen solution comprises:
$NO_3^-$ (nitrate),
$NO_2^-$ (nitrite) in a molar ratio $NO_2^-/NO_3^-$ of 0.01-0.1,
$NH_4^+$ in a molar ratio $NH_4^+/NO_3^-$ of 0.02-0.50,
$NH_2^+$ in a molar ratio $NH_2^+/NO_3^-$ of 0.0001-0.05,
other constituents in minor amounts.

The present invention further relates to a process for producing an acidic nitrate solution, suitable for reducing ammonia loss and odor from organic material or waste to the atmosphere, comprising feeding air or contaminated air to an electric arc, electrostatic field, Nano pulsed electric field, dielectric barrier discharged, laser, radio- or micro-wave driven plasma generator, or any combination thereof, to produce a concentration of 0.1-12% by volume of NOx in the air by direct nitrogen fixation;

feeding the air containing NOx to an absorber, and absorbing the NOx into an absorption liquid in the absorber to form an acidic nitrogen solution comprising:
$NO_3^-$ (nitrate),
$NO_2^-$ (nitrite) in a molar ratio $NO_2^-/NO_3^-$ of 0.01-0.1,
$NH_4^+$ in a molar ratio $NH_4^+/NO_3^-$ of 0.02-0.50,
$NH_2^+$ in a molar ratio $NH_2^+/NO_3^-$ of 0.0001-0.05,
other constituents in minor amounts.

In an embodiment, the above process comprises feeding air or contaminated air to an electric arc, electrostatic field, Nano pulsed electric field, dielectric barrier discharged, laser, radio- or micro-wave driven plasma generator, or any combination thereof, to produce a concentration of 0.1-12% by volume of NOx in the air by direct nitrogen fixation and subsequent quenching to between 60 and 150° C. within $10^{-3}$ seconds or preferably within $10^{-4}$ seconds, or most preferably $10^{-5}$ seconds; feeding the air containing NOx to an absorber after a retention time of 15 seconds to give a $NO/NO_2$ mole ratio of 3 or preferably after a retention time of 30 seconds to give a $NO/NO_2$ mole ratio of 1.2 or most preferably after a retention time of 60 seconds to get a $NO/NO_2$ mole ratio of 0.95, and absorbing the NOx into an absorption liquid in an absorber operating at a temperature between 20° C. and 80° C., or preferably between 30° C. and 60° C. to form an acidic nitrogen solution comprising:
$NO_3^-$ (nitrate),
$NO_2^-$ (nitrite) in a molar ratio $NO_2^-/NO_3^-$ of 0.01-0.1,
$NH_4^+$ in a molar ratio $NH_4^+/NO_3^-$ of 0.02-0.50,
$NH_2^+$ in a molar ratio $NH_2^+/NO_3^-$ of 0.0001-0.05,
other constituents in minor amounts.

The present invention further relates to an acidic nitrate solution, suitable for reducing ammonia loss and odor from organic material or waste to the atmosphere, comprising:
$NO_3^-$ (nitrate),
$NO_2^-$ (nitrite) in a molar ratio $NO_2^-/NO_3^-$ of 0.01-0.1,
$NH_4^+$ in a molar ratio $NH_4^+/NO_3^-$ of 0.02-0.50,
$NH_2^+$ in a molar ratio $NH_2^+/NO_3^-$ of 0.0001-0.05,
other constituents in minor amounts.

Figure 1:
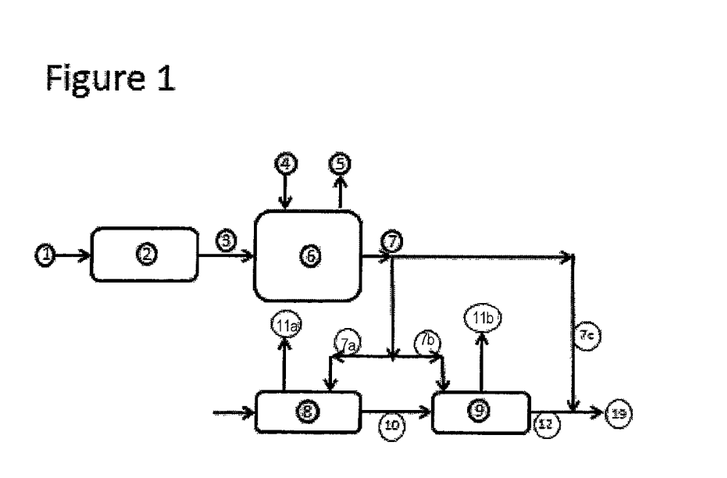
FIG. 1 shows a process according to the invention wherein the organic material or waste is directly treated with the acidic nitrogen solution.

The present invention further relates to a plant for reducing ammonia loss and odor from organic material or waste to the atmosphere, comprising a feed line (1) containing air or contaminated air; an electric arc, electrostatic field, Nano pulsed electric field, dielectric barrier discharged, laser, radio- or micro-wave driven plasma generator (2), or any combination thereof, for producing NOx in the air from the line (1); a line (3) containing the air from the generator (2); an absorber (6), having an absorption liquid inlet (4) and a scrubbed clean air outlet (5), for absorbing the NOx into the absorption liquid to form an acidic nitrogen solution comprising nitrates and nitrites; a line (7) containing the acidic nitrogen solution from the absorber (6); a source (8) of organic material or waste; an outlet (11a) containing ventilation air from the source (8); a line (10) containing the organic material or waste from the source (8); an intermediate storage (9) for storing the organic material or waste from line (10); an outlet (11b) containing ventilation air from the intermediate storage (9); a line (12) containing the organic material or waste from the intermediate storage (9); a product outlet line (19) containing the organic material or waste from line (12); and a line (7a) feeding the acidic nitrogen solution from line (7) to the source (8) and/or a line (7b) feeding the acidic nitrogen solution from line (7) to the intermediate storage (9) and/or a line (7c) feeding the acidic nitrogen solution from line (7) to the product outlet line (19).

Figure 2:
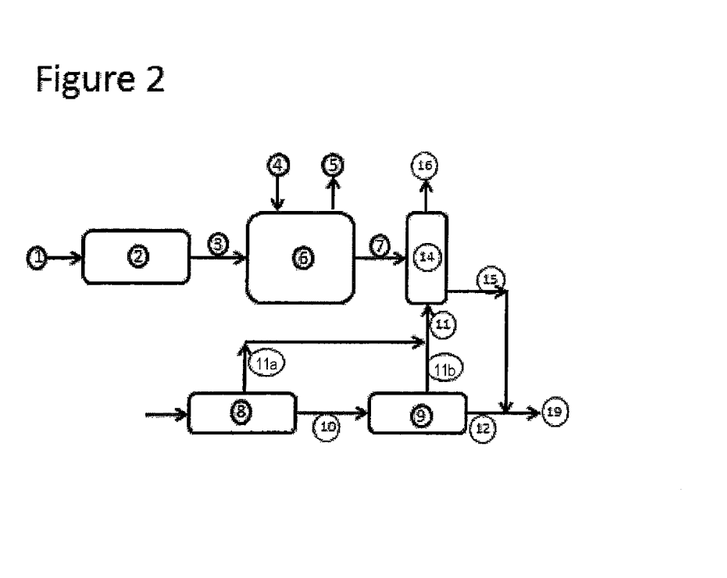
FIG. 2 shows a process according to the invention wherein ammonia in ventilation air is treated and absorbed in a scrubber using the acidic nitrogen solution before the organic material or waste is treated with the acidic nitrogen solution which after being used in the scrubber is containing the ammonia from the ventilation air.
Figure 3:
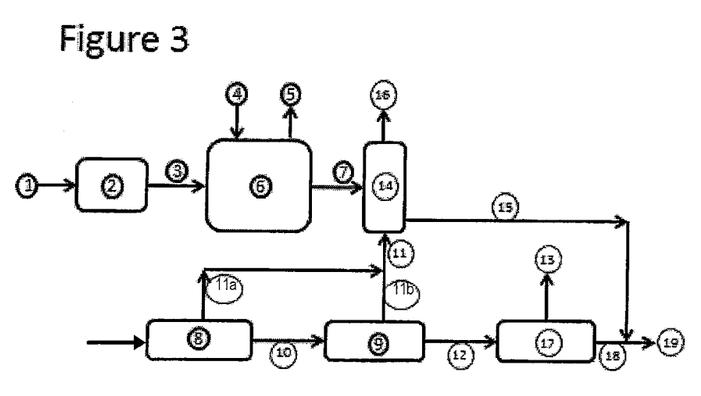
FIG. 3 shows an embodiment of the process shown in FIG. 2 wherein a bio gas reactor has been introduced.

The present invention further relates to a plant for reducing ammonia loss and odor from organic material or waste to the atmosphere, comprising a feed line (1) containing air or contaminated air; an electric arc, electrostatic field, Nano pulsed electric field, dielectric barrier discharged, laser, radio- or micro-wave driven plasma generator (2), or any combination thereof, for producing NOx in the air from the line (1); a line (3) containing the air from the generator (2); an absorber (6), having an absorption liquid inlet (4) and a scrubbed clean air outlet (5), for absorbing the NOx into the absorption liquid to form an acidic nitrogen solution comprising nitrates and nitrites; a line (7) containing the acidic nitrogen solution from the absorber (6); a source (8) of organic material or waste; an outlet (11a) containing ventilation air from the source (8); a line (10) containing the organic material or waste from the source (8); an intermediate storage (9) for storing the organic material or waste from line (10); an outlet (11b) containing ventilation air containing ammonia from the intermediate storage (9); a line (11) containing the ventilation air containing ammonia from line (11a) and line (11b); a scrubber (14) using the acidic nitrogen solution from line (7) for scrubbing ventilation air containing ammonia from line (11); a line (12) containing the organic material or waste from the intermediate storage (9); a line (15) containing an acidic ammonium nitrate and nitrite solution produced in the scrubber (14); an outlet (16) containing ammonia free air produced in the scrubber (14); a product outlet line (19) containing the organic material or waste from line (12) and the acidic ammonium nitrate and nitrite solution from line (15). This plant can also comprise a bio gas reactor (17) receiving the organic material or waste from line (12); a line (18) containing the rest from the bio gas reactor (18); and a product outlet line (19) containing the rest from the bio gas reactor (18) and the acidic ammonium nitrate and nitrite solution from line (15).

DETAILED DESCRIPTION OF THE INVENTION

The present invention is applying an electric arc, electrostatic field, Nano pulsed electric field, dielectric barrier discharged, laser, radio- or micro-wave driven plasma generator, or any combination thereof, in upgrading organic waste and manure with a mixture of acidic nitrates and nitrites. The ratio between the acidic nitrates and nitrites is controlled in the plasma process and in the absorption process through temperatures and retention times for the gas phase. The acidic nitrogen solution is reducing the ammonia and nitrogen loss and odors and is increasing the $N/P_2O_5$ ratio. The acidic nitrogen solution can be applied in scrubbing ammonia rich gasses and or directly to the organic material to bind the volatile ammonia surplus and reduce the odor formation. The composition of the acidic nitrogen solution is tailored to reduce the emission of $N_2O$. The acidity is lowering the pH which is improving the nutrient stability and plant availability of nitrogen and phosphate. The moisture content in the feed air to the plasma generator will give additional oxygen and hydrogen radicals. The hydrogen radicals will eventually form alkaline components like $NH_3$ and minor amounts and forms of $NH_2$, $NH_2^+$ and $NH$. The alkaline components preferable ammonia will enhance the nitrogen content and stabilize the nitrite.

The invention can further be used to incinerate smelly gasses by feeding them to the plasma generator. The plasma generator is sized according to the N-demand for balancing the $N/P_2O_5$ ratio in the organic material and is able to incinerate 10-50 $Nm^3$ of air per kg nitrate-N produced. For each cubic meter of pig slurry, the volume of incinerated air will typically be 50-250 $Nm^3$ and the process will add 0.2-1.0% nitrate-N to the pig slurry. The plasma technology is according to state of art able to fix nitrogen from air as NO using 30-75 GJ/tN.

The present invention is producing NO gas directly from the air in an electrically powered plasma generator at a commercially competitive cost. The plasma generator is using an electric arc or microwaves for cracking the oxygen and nitrogen molecules and forming NOx gas in air. These generators have the ability to produce different concentrations of nitrogen oxides in air. The highest practical concentration is 12% as NO formed from normal air. At this concentration, the remaining oxygen is just enough to complete the reaction from NO to $HNO_3$ in water.

$$2NO+O_2=2NO_2 \qquad\qquad II$$

$$3NO_2+H_2O=2HNO_3+NO \qquad\qquad III$$

$$4NO+3O_2+2H_2O=4HNO_3 \qquad\qquad IV=3*II+2*III$$

The azeotropic concentration of $HNO_3$ concentration is 68% and the commercial technical grade is 70%, although most industries produce 60-65% for internal use. The present invention is operating in the other end of the concentration scale for nitric acid production. The reason for operating in the highly diluted area is the nature of the process and the requirement given by the application.

In distributed on demand production, high concentrations are not required because there is no storage or transport cost. The applications for the organic components are on the contrary asking for dilute systems with tailored compositions.

In the present invention, the main effect of the acidic nitrogen solution is the reaction between the nitric acid and the free ammonia being produced from the decomposition of the organic proteins and urine. Normally 30% of the total nitrogen content is lost to air as ammonia gas because the pH of manure is normally 8-10. The acidic nitrate and nitrite solution is applied to bring the pH down to 4-6, which is stopping the ammonia losses to air.

$$HNO_3+NH_4OH=>NH_4NO_3+H_2O \qquad\qquad V$$

The acidic nitrogen solution can also be used in a scrubber for ammonia-containing ventilation air from stables or tanks instead of or in combination with direct application to the manure or organic waste. Examples of this can be when the manure or organic waste shall be fed to a biogas reactor, because the biogas reactor process may be upset by the nitrate or nitrite.

From the nitric acid technology it is known that different concentrations of nitric acid and nitrous acid can be produced depending on the temperature, pressure, retention-time for the NOx containing gas in the absorption process. The formation of nitrous oxide is more prone in dilute and cold solutions from absorption of $NO_2$ and NO gas in water. The present invention is doing the absorption at close to or below atmospheric pressure using excess cold water compared to normal nitric acid production. After the plasma generator the plasma is quenched as fast as possible by different means, like air or other suitable gasses or solid contact material sustaining the energy and temperature of the plasma. The retention time should be below $10^{-3}$ seconds, preferably below $10^{-4}$ seconds or most preferably below $10^{-5}$ seconds. After the quench the formed NOx gas in air is given a retention time at 80-120° C. for the NO gas to be converted to $NO_2$. The required retention time depends on the temperature after the quenching, but after 15 seconds the $NO/NO_2$ mole ratio is 3, and after 30 seconds the $NO/NO_2$ mole ratio is 1.2, and after 60 seconds the $NO/NO_2$ mole ratio is 0.95. In the absorption the process the reaction to $HNO_3$ is known to take place via the gas reaction II and liquid reaction III. The gas retention time in the absorber should therefore be more than 120 seconds, preferably 200 seconds, to reduce the concentration of NOx going to the air. In the present invention, the temperature of the absorber is finally used to control the ratio between nitrate and nitrite. By keeping the absorber temperature between 20-80° C., preferably 30-60° C. the concentration of $HNO_2$, can be kept in the required range. The temperature is controlling the decomposition of $HNO_2$, and can be tuned to allow enough $NO_2^-$ remain in the acid mix. See reaction VI.

$$NO+NO_2+H2O \Leftrightarrow 2HNO_2 \qquad \text{VI}$$

The nitrification (VII) and de-nitrification (VIII) process is considered to be some of the main contributors to global warming. The byproduct $N_2O$ has a global warming effect which is 320 times the effect of $CO_2$.

The concentration of nitrous acid is important as the nitrite ($NO_2^-$) is able to inhibit the microbial de-nitrification of nitrate and nitrite to $N_2$ and $N_2O$. It seems that going from $NO_3^-$ to $N_2$, the intermediate component $NO_2^-$ is inhibiting the de-nitrification if the concentration is higher than 0.01 mole/liter.

Also the nitrification bacteria are known to produce $N_2O$ in a de-nitrification process. This is probably a defense reaction to limit the toxic concentration of $NO_2^-$.

The Nitrite ($NO_2^-$) concentration is critical as it is known to effectively reduce the de-nitrification process, but it is also the component from where the $N_2O$ is produced.

The present invention is reducing the formation of $N_2O$ by lowering the pH to 4-6 and keeping a nitrite to nitrate molar ratio of 1/10 to 1/100 in order to inhibit the de-nitrification as well as the nitrification activity.

In oxygen free organic solutions, the formation of $H_2S$ is a typical reaction and indicator for odor formation. The bacteria compensate the oxygen deficiency by taking oxygen from the sulfate, converting $SO_4^{2-}$ to $H_2S$. The addition of nitrates is known to eliminate this activity and reduce the odors substantially.

The $N/P_2O_5$ demand for major crops is in the range of 2, whereas the $N/P_2O_5$ ratio in manure is lower than this. The present technology is both adding nitrogen and reducing the loss of nitrogen. The target ratio is approached by dosing the acidic nitrogen solution according to the formation of free ammonia from the biological activity. It may also be possible to stop the biological activity through overdosing and lowering the pH. The capacity of the plasma generator and acidic nitrogen solution production is controlled by increasing the power input. This will give higher NO concentration in the air passing through the plasma generator.

The present technology is also able to improve the plant availability of phosphate in organic waste from water purification systems. The reason for initial low availability is that the phosphates are chemically precipitated with Mg, Al, Ca or Fe at high pH to the form the components with the lowest solubility. The intensity of the precipitation is forming colloidal precipitates which require flocculation. The present invention is able to improve the solubility of the phosphates through a temporary lowering of the pH and thereafter letting the chemical and biological reactions mobilize the phosphates in a slightly acidic environment.

In an embodiment, the present invention relates to a process for reducing ammonia loss and odor from organic material or waste to the atmosphere, comprising feeding air or contaminated air to an electric arc, electrostatic field, Nano pulsed electric field, dielectric barrier discharged, laser, radio- or micro-wave driven plasma generator, or any combination thereof, to produce a concentration of 0.1-12% by volume of NOx in the air by direct nitrogen fixation and subsequent quenching within $10^{-3}$ seconds, preferably $10^{-4}$ seconds or most preferably $10^{-5}$ seconds. After the quench the formed NOx gas in air is given a retention time at 80-120° C. for the NO gas to be converted to $NO_2$. The required retention time depends on the temperature after the quenching, but after 15 seconds the $NO/NO_2$ mole ratio is 3, and after 30 seconds the $NO/NO_2$ mole ratio is 1.2, and after 60 seconds the $NO/NO_2$ mole ratio is 0.95, before further absorbing the NOx into an absorption liquid in an absorber operating at 20-80° C., preferably 30-60° C. to form an acidic nitrogen solution comprising nitrates and nitrites as well as some ammonia and minor amounts of alkaline nitrogen compounds; and feeding the acidic nitrogen solution to the organic material or waste whereby the pH is adjustted to 4-6 and the nitrates and nitrites bind volatile ammonia and ammonia components in or from the organic material or waste, as ammonium nitrate and nitrite salts. In this process, the acidic nitrogen solution can be passed through a scrubber to absorb ammonia from ammonia contaminated ventilation air from the organic material or waste.

In a further embodiment, the present invention relates to a process for reducing ammonia loss and odor from organic material or waste to the atmosphere, comprises feeding air or contaminated air to an electric arc, electrostatic field, Nano pulsed electric field, dielectric barrier discharged, laser, radio- or micro-wave driven plasma generator, or any combination thereof, to produce a concentration of 0.1-12% by volume of NOx in the air by direct nitrogen fixation and subsequent quenching within $10^{-3}$ seconds, preferably below $10^{-4}$ seconds or most preferably $10^{-5}$ seconds. After the quench the formed NOx gas in air is given a retention time at 80-120° C. for the NO gas to be converted to $NO_2$.

The required retention time depends on the temperature after the quenching, but after 15 seconds the $NO/NO_2$ mole ratio is 3, and after 30 seconds the $NO/NO_2$ mole ratio is 1.2, and after 60 seconds the $NO/NO_2$ mole ratio is 0.95 before absorbing the NOx in an absorber operating at 20-80° C. preferably 30-60° C., to form an acidic nitrogen solution comprising nitrates and nitrites; using the acidic nitrogen solution in a scrubber to absorb ammonia from ammonia contaminated ventilation air from the organic material or waste and to produce an acidic ammonium nitrate and nitrite solution; and feeding the acidic ammonium nitrate and nitrite solution produced in the scrubber to the organic material or waste. In this process, the organic material or waste can be treated in a bio gas reactor before feeding the acidic ammonium nitrate and nitrite solution produced in the scrubber to the organic material or waste.

FIG. 1 is showing the basic principle of the invention. Air 1 is fed to the plasma generator 2. The outlet 3 of the plasma generator is a mix of nitrogen oxides in air. Flow 3 is entering the absorber 6. In the absorber 6 the nitrogen oxides are absorbed in water 4 which is entering the top of the absorber. The scrubbed clean air 5 is released to the atmosphere. The liquid leaving the bottom of the absorber 7 is a mix of acidic nitrogen oxides, mainly nitrates and nitrites. The absorption liquid 4 can also be urine containing ammonium, and in this case the liquid outlet 7 will also contain acidic ammonium nitrate and nitride. The acidic liquid with the right composition of nitrate and nitrite 7 is then applied to the manure or organic waste where practically suitable and preferably several places from the source to the final outlet. It can be applied directly to the stables 8 where it will reduce the ammonia emissions and odors in the stables and in the ventilation air 11a. The acidic nitrogen flow 7a will also increase the nitrogen content in the flow of manure or organic waste 10 going to the intermediate storage 9. The intermediate storage 9 can also be treated with the acidic nitrogen solution 7b to neutralize the ammonia being released in the fermentation and mineralization of the manure or organic waste in the intermediate storage 9. The effect will be less ammonia in the ventilation air 11b and a higher nitrogen content in the outlet 12. The outlet 12 of the intermediate storage 9 can also be given a final treatment of the acidic nitrogen solution 7c in order to adjust the nitrogen and or pH before transport and spreading.

FIG. 2 is demonstrating another principle for how the invention can reduce ammonia losses and odors and increase the nitrogen content in manure or organic waste. Air 1 is fed to the plasma generator 2. The outlet 3 of the plasma generator is a mix of nitrogen oxides in air. Flow 3 is entering the absorber 6. In the absorber 6 the nitrogen oxides are absorbed in water 4 which is entering the top of the absorber. The scrubbed clean air 5 is released to the atmosphere. The liquid leaving the bottom of the absorber 7 is a mix of acidic nitrogen oxides, mainly nitrates and nitrites. In this technique the acidic nitrogen solution 7 is used in a ventilation air scrubber 14. The ventilation air scrubber technique can be installed as a standalone principle, or combined with the direct application to the manure or organic waste as described in FIG. 1. The ventilation air 11a from the stables 8 and the ventilation air 11b from the intermediate storage 9 are directed as feed 11 to the scrubber 14. The scrubber outlet 16 will be ammonia free air, and the liquid outlet 15 will be an acidic ammonium nitrate and nitrite solution. The acidic ammonium nitrate and nitrite solution 15 is applied directly to the manure or organic outlet 12 from the intermediate storage in order to upgrade the nutrient value of the final product 19. The effect will be also reduce further losses of ammonia and nitrous oxide.

FIG. 3 is showing how the invention is applied to a situation comprising a biogas reactor. Air 1 is fed to the plasma generator 2. The outlet 3 of the plasma generator is a mix of nitrogen oxides in air. Flow 3 is entering the absorber 6. In the absorber 6 the nitrogen oxides are absorbed in water 4 which is entering the top of the absorber. The scrubbed clean air 5 is released to the atmosphere. The liquid leaving the bottom of the absorber 7 is a mix of acidic nitrogen oxides, mainly nitrates and nitrites. In this technique the acidic nitrogen solution 7 is used in a ventilation air scrubber 14. Direct application of acidic nitrogen solution 7 to the manure and or organic waste before it is fed to the biogas reactor may not be beneficial to the biogas reactor. The ventilation air 11a from the stables or source of the organic waste 8 and the ventilation air 11b from the intermediate storage 9 are directed as feed 11 to the ventilation air scrubber 14. The feed 10 to the intermediate storage and the feed 12 to the bio gas reactor 17 will be untreated with nitrates and nitrites, in order not to disturb the quality of the bio gas 13. The air outlet 16 from the scrubber 14 will be ammonia free air, and the liquid outlet 15 will be an acidic ammonium nitrate and nitrite solution. The acidic ammonium nitrate and nitrite solution 15 is applied to the bio-rest 18 from the bio gas reactor 17. The final bio gas rest 19 will be upgraded with nitrogen and pH controlled to limit further losses of ammonia and nitrous oxide.

The invention claimed is:

1. A process for reducing ammonia loss and odor from organic material or waste to the atmosphere, comprising
   feeding air or contaminated air to an electric arc, electrostatic field, Nano pulsed electric field, dielectric barrier discharged, laser, radio- or micro-wave driven plasma generator, or any combination thereof, to produce a concentration of 0.1-12% by volume of NOx in the air by direct nitrogen fixation and subsequent quenching to between 60° C. and 150° C. within $10^{-3}$ seconds;
   feeding the air containing NOx to an absorber, and absorbing the NOx into an absorption liquid in the absorber operating at a temperature between 20° C. and 80° C. to form an acidic nitrogen solution comprising nitrates and nitrites; and
   feeding the acidic nitrogen solution to the organic material or waste whereby the pH is adjusted to 4-6 and the nitrates and nitrites bind volatile ammonia and ammonia components in or from the organic material or waste, as ammonium nitrate and nitrite salts.

2. The process according to claim 1, comprising feeding air or contaminated air to an electric arc, electrostatic field, Nano pulsed electric field, dielectric barrier discharged, laser, radio- or micro-wave driven plasma generator, or any combination thereof, to produce a concentration of 0.1-12% by volume of NOx in the air by direct nitrogen fixation and subsequent quenching to between 60° C. and 150° C. within $10^{-4}$ seconds; feeding the air containing NOx to an absorber after a retention time of 15 seconds to give a $NO/NO_2$ mole ratio of 3, and absorbing the NOx into an absorption liquid in an absorber operating at a temperature between 30° C. and 60° C. to form an acidic nitrogen solution comprising nitrates and nitrites; and feeding the acidic nitrogen solution to the organic material or waste whereby the pH is adjusted to 4-6 and the nitrates and nitrites bind volatile ammonia and ammonia components in or from the organic material or waste, as ammonium nitrate and nitrite salts.

3. The process according to claim 1, wherein the acidic nitrogen solution is passed through a scrubber to absorb ammonia from ammonia contaminated ventilation air from the organic material or waste.

4. A process for reducing ammonia loss and odor from organic material or waste to the atmosphere, comprising
feeding air or contaminated air to an electric arc, electrostatic field, Nano pulsed electric field, dielectric barrier discharged, laser, radio- or micro-wave driven plasma generator, or any combination thereof, to produce a concentration of 0.1-12% by volume of NOx in the air by direct nitrogen fixation and subsequent quenching to between 60° C. and 150° C. within $10^{-3}$ seconds;
feeding the air containing NOx to an absorber, and absorbing the NOx into an absorption liquid in the absorber operating at a temperature between 20° C. and 80° C. to form an acidic nitrogen solution comprising nitrates and nitrites;
using the acidic nitrogen solution in a scrubber to absorb ammonia from ammonia contaminated ventilation air from the organic material or waste and to produce an acidic ammonium nitrate and nitrite solution; and
feeding the acidic ammonium nitrate and nitrite solution produced in the scrubber to the organic material or waste.

5. The process according to claim 4, comprising feeding air or contaminated air to an electric arc, electrostatic field, Nano pulsed electric field, dielectric barrier discharged, laser, radio- or micro-wave driven plasma generator, or any combination thereof, to produce a concentration of 0.1-12% by volume of NOx in the air by direct nitrogen fixation and subsequent quenching to between 60° C. and 150° C. within $10^{-4}$ seconds; feeding the air containing NOx to an absorber, after a retention time of 15 seconds to give a NO/NO$_2$ mole ratio of 3, and absorbing the NOx into an absorption liquid in an absorber operating at a temperature between 30° C. and 60° C. to form an acidic nitrogen solution comprising nitrates and nitrites; using the acidic nitrogen solution in a scrubber to absorb ammonia from ammonia contaminated ventilation air from the organic material or waste and to produce an acidic ammonium nitrate and nitrite solution; and feeding the acidic ammonium nitrate and nitrite solution produced in the scrubber to the organic material or waste.

6. The process according to claim 4, wherein the organic material or waste is treated in a bio gas reactor before feeding the acidic ammonium nitrate and nitrite solution produced in the scrubber to the organic material or waste.

7. The process according to claim 1, wherein air or contaminated air is fed to the plasma generator to produce a concentration of 2-12% by volume of NOx in the air by direct nitrogen fixation.

8. The process according to claim 1, wherein the absorption liquid is water or urine.

9. The process according to claim 1, wherein the absorption liquid is cold water in excess.

10. The process according to claim 1, wherein the organic material or waste is selected from livestock manure and biogas plant rest.

11. The process according to claim 1, wherein the nitrate and nitrite components are providing oxygen which suppresses the activity of sulfate reduction to $H_2S$.

12. The process according to claim 1, wherein the nitrate and nitrite ratio in combination with a pH of 4-6 is used to disinfect organic materials or waste.

13. The process according to claim 1, wherein the molar ratio of nitrite to nitrate is kept between 1/10 and 1/100 which is inhibiting $N_2O$ being formed in the biological nitrification of ammonia.

14. The process according to claim 1, wherein the molar nitrate concentration is balancing the molar free ammonia-N concentration to improve the plant uptake rate of nitrogen.

15. The process according to claim 1, wherein the plasma generator is used to incinerate and disinfect contaminated air by exposing the contaminants to plasma and electron bombardment.

16. The process according to claim 1, wherein the nitrate and nitrite solution is used to improve the agronomic availability of the phosphate, through a temporary lowering of pH to 4 which is dissolving and mobilizing the colloidal phosphates precipitates.

17. The process according to claim 1, wherein the acidic nitrogen solution comprises:
$NO_3^-$ (nitrate),
$NO_2^-$ (nitrite) in a molar ratio $NO_2^-/NO_3^-$ of 0.01-0.1,
$NH_4^+$ in a molar ratio $NH_4^+/NO_3^-$ of 0.02-0.50,
$NH_2^+$ in a molar ratio $NH_2^+/NO_3^-$ of 0.0001-0.05,
other constituents in minor amounts.

* * * * *